(12) United States Patent
Kapelewski et al.

(10) Patent No.: US 11,453,622 B2
(45) Date of Patent: Sep. 27, 2022

(54) CATALYTIC CONVERSION OF ALCOHOLS AND/OR ETHERS TO OLEFINS

(71) Applicant: ExxonMobil Technology and Engineering Company, Annandale, NJ (US)

(72) Inventors: Matthew T. Kapelewski, Flemington, NJ (US); Lei Zhang, Basking Ridge, NJ (US); Brandon J. O'Neill, Lebanon, NJ (US)

(73) Assignee: EXXONMOBIL TECHNOLOGY AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 17/060,120

(22) Filed: Oct. 1, 2020

(65) Prior Publication Data

US 2022/0106239 A1  Apr. 7, 2022

(51) Int. Cl.
| | | |
|---|---|---|
| C07C 1/24 | (2006.01) | |
| B01J 29/40 | (2006.01) | |
| C07C 2/12 | (2006.01) | |
| B01J 29/90 | (2006.01) | |
| B01J 8/08 | (2006.01) | |

(52) U.S. Cl.
CPC .................. *C07C 1/24* (2013.01); *B01J 8/082* (2013.01); *B01J 29/405* (2013.01); *B01J 29/90* (2013.01); *C07C 2/12* (2013.01); *B01J 2208/00017* (2013.01); *B01J 2208/00539* (2013.01)

(58) Field of Classification Search
CPC .... C07C 1/24; C07C 2/12; B01J 8/082; B01J 29/405; B01J 29/90; B01J 2208/00017; B01J 2208/00539
See application file for complete search history.

(56) References Cited

U.S. PATENT DOCUMENTS

2017/0137720 A1\* 5/2017 Harandi .................. B01J 29/80

OTHER PUBLICATIONS

Ilias et al., "Mechanism of the Catalytic Conversion of Methanol to Hydrocarbons", ACS Catal. 2013, 3, 18-31.
Johansson et al., "The Hydrocarbon Pool in Ethanol-to-Gasoline over HZSM-5 Catalysts", Catalysis Letters 2009, 127, 1-6.
Narula et al., "Heterobimetallic Zeolite, InV-ZSM-5, Enables Efficient Conversion of Biomass Derived Ethanol to Renewable Hydrocarbons", Scientific Reports 2015, 5, 1-9.

\* cited by examiner

*Primary Examiner* — Ali Z Fadhel
(74) *Attorney, Agent, or Firm* — Kristina Okafor

(57) ABSTRACT

Processes for the catalytic conversion of alcohols and/or ethers to olefins over zeolite catalysts are described. Self-bound ZSM-5 and metal containing variants, such as Zn ZSM-5, produce high yields of olefins, particularly C3+ olefins, between 250 and 450° C.

24 Claims, 7 Drawing Sheets

CATALYTIC CONVERSION OF ALCOHOLS AND/OR ETHERS TO OLEFINS

FIELD OF THE INVENTION

This disclosure relates to catalytic conversion of alcohols and/or ethers to olefins over zeolite based conversion catalysts. In particular the disclosure relates to catalytic conversion of alcohols and/or ethers over zeolite based conversion catalysts with high yields to C3+ olefins.

BACKGROUND OF THE INVENTION

Conversion of methanol to olefins and other unsaturated compounds is a commonly used reaction scheme for chemical manufacture. Conventional methods can involve exposing a methanol-containing feed to a molecular sieve, such as ZSM-5 or SAPO-34.

Alcohols, especially those produced from biological sources, are potential alternatives to petroleum-based fuels. For example, ethanol can be derived from the fermentation of biological feedstocks, as well as the bio-conversion of waste streams from steel manufacturing and of municipal solid waste. As ethanol is not a drop-in replacement for gasoline or diesel, however, it must be further upgraded to be used as a fuel in most applications.

Narula C. K. et al (Scientific Reports volume 5, Article number: 16039, 2015) describe the conversion of ethanol to olefins over an InV-ZSM-5 zeolite. The catalyst converts ethanol at 360° C. to 6.5% olefins, 33.2% paraffins, and 60.2% aromatics.

In view of the foregoing, it would be desirable to provide improved catalysts and processes for the conversion of oxygenates such as alcohols or ethers to olefins.

The reference in this specification to any prior publication (or information derived from it), or to any matter which is known, is not, and should not be taken as an acknowledgement or admission or any form of suggestion that the prior publication (or information derived from it) or known matter forms part of the common general knowledge in the field of endeavour to which this specification relates.

SUMMARY OF THE INVENTION

The present disclosure relates to novel processes for converting alcohols and/or ethers to olefins.

In one aspect the present disclosure provides a process for converting alcohols and/or ethers to olefins, said process comprising:
contacting a feed comprising one or more alcohols and/or one or more ethers with a conversion catalyst in a reaction zone at a temperature from about 200° C. to about 550° C. under conditions effective to produce an olefin-containing effluent, the olefin-containing effluent comprising 10 wt. % or more of olefins, and 60 wt. % or less of aromatics relative to a weight of hydrocarbons in the olefin-containing effluent, the olefin-containing effluent comprising 5 wt. % or more of C3+ olefins relative to a weight of hydrocarbons in the olefin-containing effluent, the conversion catalyst comprising a zeolite framework structure.

In embodiments, the wt. % of olefins relative to the weight of hydrocarbons in the olefin-containing effluent is 15 wt. % or more, or 20 wt. % or more, or 25 wt. % or more, or 30 wt. % or more, or 35 wt. % or more, or 40 wt. % or more, or 45 wt. % or more, or 50 wt. % or more, or 55 wt. % or more.

In embodiments, the wt. % of aromatics relative to the weight of hydrocarbons in the olefin-containing effluent is 40 wt. % or less, or 35 wt. % or less, or 30 wt. % or less, or 25 wt. % or less.

In embodiments, the wt. % of C3+ olefins relative to the weight of hydrocarbons in the olefin-containing effluent is 10 wt. % or more, or 15 wt. % or more, or 20 wt. % or more, or 25 wt. % or more, or 30 wt. % or more, or 35 wt. % or more.

In embodiments, the wt. % of C4+ olefins relative to the weight of hydrocarbons in the olefin-containing effluent is 10 wt. % or more, or 15 wt. % or more, or 20 wt. % or more, or 25 wt. % or more, or 30 wt. % or more, or 35 wt. % or more.

In embodiments, the wt. % of paraffins relative to the weight of hydrocarbons in the olefin-containing effluent is 45 wt. % or less, or 40 wt. % or less, or 35 wt. % or less, or 30 wt. % or less, or 25 wt. % or less, or 20 wt. % or less, or 15 wt. % or less, or 10 wt. % or less.

In some embodiments, the contacting occurs at a temperature from about 250° C. to about 550° C., or from about 300° C. to about 500° C.

In some embodiments, the contacting occurs at a pressure from about 10 psig to about 400 psig, or from about 10 psig to about 100 psig.

In some embodiments, the WHSV is from about 0.1 $h^{-1}$ to about 10 $h^{-1}$, or from about 0.5 $h^{-1}$ to about 5 $h^{-1}$.

In embodiments, the conversion catalyst comprises an MFI type zeolite.

In some embodiments, the conversion catalyst comprises ZSM-5.

In other embodiments, the conversion catalyst comprises silicalite.

In some embodiments, the conversion catalyst comprises a self-bound zeolite.

In alternate embodiments, the conversion catalyst further comprises about 1 wt. % to about 40 wt. % of a binder, for example a binder comprising one or more of $Al_2O_3$, $TiO_2$, $ZrO_2$, $SiO_2$, $SiO_2/Al_2O_3$, and MgO, based on the total weight of the conversion catalyst.

In embodiments, the conversion catalyst further comprises about 0.1 wt. % to about 20 wt. % of one or more metals selected from groups 1 to 14 of the periodic table.

In embodiments, the conversion catalyst further comprises about 0.1 wt. % to about 20 wt. % of one or more metals selected from groups 12 to 14 of the periodic table.

In embodiments, the conversion catalyst further comprises about 0.1% to about 5 wt. % of one or more metals selected from groups 12 to 14 of the periodic table.

In embodiments, the conversion catalyst further comprises about 0.1 wt. % to about 20 wt. % of one or more metals selected from groups 1 or 2 of the periodic table.

In embodiments, the conversion catalyst further comprises about 0.1% to about 5 wt. % to of one or more metals selected from groups 1 or 2 of the periodic table.

In embodiments, the one or more metals comprise one or more of Zn, Ga, B, Ca, Ti, V, Fe, Cu, Mo, Ru, Pd, Rh, Ir, Nb, W, Re, and Pt.

In embodiments, the conversion catalyst comprises Zn. In some embodiments, the conversion catalyst comprises about 0.1 wt. % to about 2 wt. % Zn.

In embodiments, the reaction zone comprises one or more of a fixed bed reactor, a fluidized bed reactor, a riser reactor, and a moving bed reactor. Preferred reactors include a moving bed reactor or a fixed bed reactor.

A feature of the present disclosure is that as a conversion catalyst is exposed to increasing amounts of alcohol and/or ether containing feed, the relative yields of products in the olefin-containing effluent may change. Without wishing to be bound by theory this is likely due to a build up of carbonaceous material in the conversion catalyst.

As certain desirable products may have high yields only after being exposed to a particular amount of alcohol and/or ether containing feed, operating the reaction zone so that it comprises conversion catalyst which has been exposed to a particular amount of feed advantageously may lead to high yields of desirable products. This may be achieved through catalyst regeneration strategies which regulate the average conversion catalyst exposure to alcohol and/or ether.

In other words, the observation that relative product yields may change with time on stream may be advantageously utilized to control or maximize the yield of particular products, for example C3+ olefins.

In embodiments, wherein the reaction zone comprises a moving bed reactor, the process further comprises a step of transferring at least a portion of the conversion catalyst to a regeneration zone, separate from the reaction zone, and contacting the conversion catalyst with a regeneration gas in the regeneration zone to at least partially remove coke deposited on the conversion catalyst in the reaction zone, whereby the conversion catalyst is at least partially regenerated, and then returning the thus at least partially regenerated conversion catalyst to the reaction zone.

In some embodiments, the at least partially regenerated conversion catalyst is returned to the reaction zone at a rate sufficient to produce an olefin-containing effluent comprising 10 wt. % or more of C3+ olefins, relative the weight of hydrocarbons in the olefin-containing effluent The at least partially regenerated conversion catalyst may be returned to the reaction zone at a rate sufficient to produce an olefin-containing effluent comprising 15 wt. % or more of C3+ olefins, or 20 wt. % or more, or 25 wt. % or more, or 30 wt. % or more, or 35 wt. % or more, relative the weight of hydrocarbons in the olefin-containing effluent.

In additional or alternate embodiments, the at least partially regenerated conversion catalyst is returned to the reaction zone at a rate sufficient so that, 1 gram of conversion catalyst is, on average, exposed to at least 200 gram of feed in the reaction zone.

The at least partially regenerated conversion catalyst may be returned to the reaction zone at a rate sufficient so that 1 gram of conversion catalyst is, on average, exposed to at least 300 gram of feed, or at least 400 gram of feed, or at least 500 gram of feed in the reaction zone.

In additional or alternate embodiments, the at least partially regenerated conversion catalyst is returned to the reaction zone at a rate sufficient to afford an average degree of conversion catalyst coking within the reaction zone to produce an olefin-containing effluent comprising 10 wt. % or more of C3+ olefins, relative the weight of hydrocarbons in the olefin-containing effluent.

The at least partially regenerated conversion catalyst may be returned to the reaction zone at a rate sufficient to afford an average degree of conversion catalyst coking within the reaction zone to produce an olefin-containing effluent comprising 15 wt. % or more of C3+ olefins, or 20 wt. % or more, or 25 wt. % or more, or 30 wt. % or more, or 35 wt. % or more, relative the weight of hydrocarbons in the olefin-containing effluent.

In embodiments, the regeneration gas comprises oxygen. In some embodiments, the regeneration gas may be air.

In embodiments, the regeneration zone comprises one or more of a riser reactor, a moving bed reactor or a fixed bed reactor.

In embodiments, the one or more alcohols comprise one or more of ethanol, 1-propanol, 2-propanol, 1-butanol and 2-butanol.

In embodiments, the one or more alcohols may be derived from fermentation or bio-conversion. In alternate or additional embodiments, the one or more alcohols may be derived from the conversion of synthesis gas.

In embodiments, the one or more alcohols may further comprise water.

In embodiments, the feed comprising one or more alcohols comprises at least 5% by weight of the one or more alcohols.

In embodiments, the one or more ethers comprise one or more of diethyl ether, di-n-propyl ether, di-iso-propyl ether, di-n-butyl ether and di-iso-butyl ether.

In some embodiments, the process further comprises the step of separating water from the olefin-containing effluent.

In some embodiments, the process further comprises the step of separating at least some of the olefin-containing effluent to provide a stream rich in olefins.

In some embodiments, the process further comprises the step of separating at least some of the stream rich in olefins to provide at least a stream rich in ethylene and a stream rich in C3+ olefins.

In some embodiments, the stream rich in ethylene is further processed, for example, oligomerized to higher olefins.

In some embodiments, at least some of the C3+ olefins are oligomerized to higher olefins, and, optionally, further hydrogenated to jet or diesel fuels.

Advantages of the processes disclosed herein may include one or more of the following:
  high alcohol and/or ether conversion;
  high yields of olefins including high yields of C3+ or C4+ olefins;
  ability to select operating conditions through the use of, for example, moving bed reactors to maximise or control the yields of particular products.

Further features and advantages of the present disclosure will be understood by reference to the following drawings and detailed description.

DETAILED DESCRIPTION OF THE EMBODIMENTS

Figure 1:
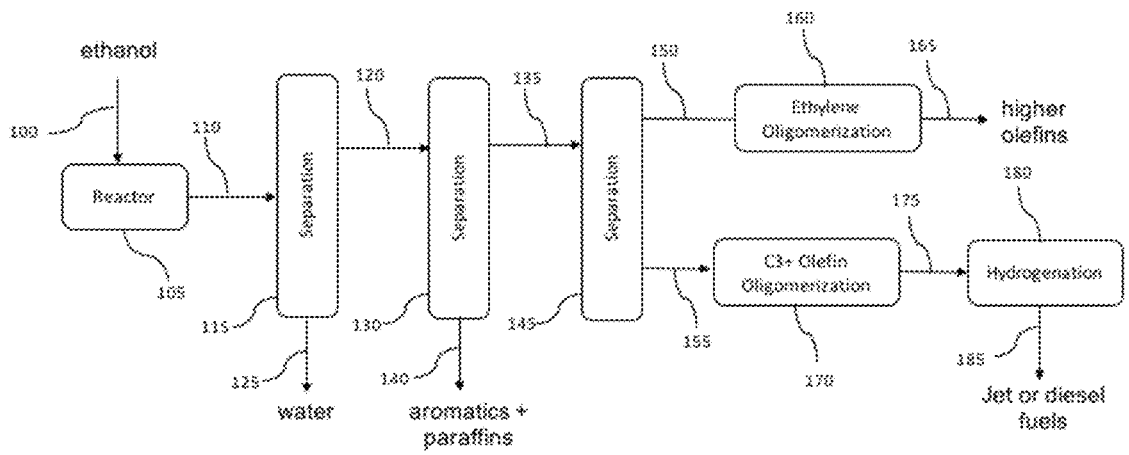
FIG. 1 is a flowsheet showing a process according to an embodiment of the present disclosure.

The following is a detailed description of the present disclosure provided to aid those skilled in the art in practicing the disclosure. Those of ordinary skill in the art may make modifications and variations in the embodiments described herein without departing from the spirit or scope of the present disclosure.

Although any processes and materials similar or equivalent to those described herein can also be used in the practice or testing of the present disclosure, the preferred processes and materials are now described.

It must also be noted that, as used in the specification and the appended claims, the singular forms 'a', 'an' and 'the' include plural referents unless otherwise specified. Thus, for example, reference to 'olefin' may include more than one olefins, and the like.

Throughout this specification, use of the terms 'comprises' or 'comprising' or grammatical variations thereon shall be taken to specify the presence of stated features, integers, steps or components but does not preclude the presence or addition of one or more other features, integers, steps, components or groups thereof not specifically mentioned.

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as Hawley's Condensed Chemical Dictionary 14th Edition, by R. J. Lewis, John Wiley & Sons, New York, N.Y., 2001.

Unless specifically stated or obvious from context, as used herein, the term "about" is understood as within a range of normal tolerance in the art, for example within two standard deviations of the mean. 'About' can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein in the specification and the claim can be modified by the term 'about'.

Any processes provided herein can be combined with one or more of any of the other processes provided herein.

Ranges provided herein are understood to be shorthand for all of the values, including non-integer values, within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein the term 'moving bed' reactor means a zone or vessel with contacting of solids and gas flows such that the superficial gas velocity (U) is below the velocity required for dilute-phase pneumatic conveying of solid particles in order to maintain a solids bed with void fraction below 95%. A moving-bed reactor may operate under several flow regimes including settling or moving packed-bed regime ($U<U_{mf}$), bubbling regime ($U_{mf}<U<U_{mb}$), slugging regime ($U_{mb}<U<U_c$), transition to and turbulent fluidization regime ($U_c<U<U_{tr}$), and fast-fluidization regime ($U>U_{tr}$). As used herein '$U_{mf}$' is the minimum fluidization velocity, '$U_{mb}$' is the minimum bubbling velocity, '$U_c$' is the onset velocity for the transition to turbulent fluidization, and '$U_{tr}$' is the transport velocity. These different fluidization regimes have been described in, for example, Kunii, D., Levenspiel, O., Chapter 3 of Fluidization Engineering, 2" Edition, Butterworth-Heinemann, Boston, 1991.

As used herein the term 'fluidized bed' reactor means a zone or vessel with contacting of solids and gas flows such that the superficial gas velocity (U) is sufficient to fluidize solid particles (i.e., above the minimum fluidization velocity $U_{mf}$) and is below the velocity required for dilute-phase pneumatic conveying of solid particles in order to maintain a solids bed with void fraction below 95%. Minimum fluidization velocity is discussed in, for example, the Kunii publication noted above.

As used herein the term 'riser reactor' means a zone or vessel (such as a vertical cylindrical pipe) used for net upwards transport of solids in fast-fluidization or pneumatic conveying fluidization regimes. Fast fluidization and pneumatic conveying fluidization regimes are characterized by superficial gas velocities (U) greater than the transport velocity ($U_{tr}$). Fast fluidization and pneumatic conveying fluidization regimes are also described in the Kunii publication noted above.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims.

Overview

The present disclosure describes the use of zeolite based conversion catalysts, such as 'self-bound' SB-ZSM-5, and metal containing SB-ZSM-5, such as Zn SB-ZSM-5, for the advantaged conversion of alcohols and/or ethers to olefins. The SB-ZSM-5 advantageously compares with leading ethanol conversion catalyst from the literature (InV-ZSM-5), even though it contains no expensive added transition metals, while the Zn SB-ZSM-5 has a significantly advantaged selectivity to producing olefins over both InV-ZSM-5 and SB-ZSM-5. The Zn SB-ZSM -5 also has the advantage of producing about 35% C3+ olefins between 250 and 450° C., significantly more than that produced by either of the other materials. Both SB-ZSM-5 and Zn SB-ZSM -5 represent advantaged conversion catalysts for the production of olefins.

In various embodiments, a conversion catalyst comprising a suitable zeotype framework material (such as a zeolitic material) can be used for conversion of alcohols and/or ethers to olefins. In some embodiments, an optionally metal-enhanced zeotype conversion catalyst, such as a conversion catalyst including a Zn-enhanced zeotype framework material, may be used for the conversion of alcohols and/or ethers to olefins.

As used herein, a zeotype refers to a crystalline material having a porous framework structure built from tetrahedral atoms connected by bridging oxygen atoms. Examples of known zeotype/zeolite frameworks are given in the "Atlas of Zeolite Frameworks" published on behalf of the Structure Commission of the International Zeolite Association, 6th revised edition, Ch. Baerlocher, L. B. McCusker, D. H. Olson, eds., Elsevier, New York (2007) and the corresponding web site, http://www.iza-structure.org/databases/. Under this definition, a zeolite can refer to aluminosilicates having a zeotype framework type as well, while a zeotype more generally refers crystalline structures having a suitable framework structure that may contain oxides of Si, Al, and/or heteroatoms different from Si and Al. Such heteroatoms can include any heteroatom generally known to be suitable for inclusion in a zeotype framework, such as gallium, boron, germanium, phosphorus, zinc, and/or other transition metals that can substitute for silicon and/or aluminum in a zeotype framework.

As used herein, a Cx hydrocarbon, alcohol, olefin, oxygenate, or other compound, or of a carbon chain in such a compound, is a reference to a compound (or carbon chain in such a compound) that contains the specified number of carbons. Ethanol is an example of a C2 alcohol. C3+ is an example of one or more chemical compounds, for example one or more olefins, having three or more carbon atoms. A reference to a stream or fraction containing Cx-Cy compounds corresponds to a stream or fraction that contains at least one component having a carbon backbone with x carbons, y carbons, or a number of carbons between x and y. For example, a stream containing C3-C6 olefins corresponds to a stream containing at least one of C3 olefins, C4 olefins, C5 olefins, or C6 olefins.

Feedstocks and Products

In various embodiments, conversion catalysts described herein can be used for conversion of alcohol and/or ether containing feeds to olefins. In embodiments, the feeds may comprise one or more alcohols, one or more ethers or one or more alcohols and one or more ethers. In some embodiments, the alcohols may comprise one or more of ethanol, 1-propanol, 2-propanol, 1-butanol and 2-butanol. In some embodiments, the ethers may comprise one or more of diethyl ether, di-n-propyl ether, di-iso-propyl ether, di-n-butyl ether and di-iso-butyl ether.

Preferably an ethanol containing feed can include 3 wt. % or more of ethanol, or 5 wt. % or more of ethanol, or 10 wt. % or more of ethanol, or 20 wt. % or more of ethanol, or 30 wt. % or more of ethanol, or 50 wt. % or more, or 75 wt. % or more, or 90 wt. % or more, or at least 95 wt. %. The ethanol may be derived from any convenient source. The ethanol may be produced from biological sources, such as by fermentation or bio-conversion.

In addition to alcohols and/or ethers, a feed can also include diluents, such as water (in liquid or gaseous form), nitrogen or other inert gases, and/or paraffins or other non-reactive hydrocarbons. Optionally, at least a portion of such diluents can be removed prior to exposing the alcohol to a conversion catalyst. Optionally, the feed can further include olefins, such as 10 wt. % or less of olefins, or 5 wt. % or less. Such optional olefins can, for example, correspond to C2-C6 olefins, such as having 70 wt. % or more of the olefins correspond to C2-C3 olefins, or such as having 50 wt. % or more of the olefins correspond to C3-C6 olefins. In such optional aspects, 10 wt. % or less of the olefins can correspond to C7+ olefins, or 5 wt. % or less, or 1 wt. % or less.

In various embodiments, alcohols and ethers may be converted into olefins in the presence of a conversion catalyst under conversion conditions.

The conversion catalyst may comprise a zeolite (or other zeotype) in its original crystalline form or after formulation into catalyst extrudates, such as by extrusion.

In some embodiments the catalyst particles are self-bound catalyst particles. The term "self-bound" means that the conversion catalyst is free of any binder, for example inorganic oxide binders, such as one or more of $Al_2O_3$, $TiO_2$, $ZrO_2$, $SiO_2$, $SiO_2/Al_2O_3$, and MgO, frequently combined with zeolite catalysts to enhance their physical properties.

One example of binding zeolite crystals to form catalyst particles is to form a self-bound catalyst. A process for producing zeolite extrudates in the absence of a binder is disclosed in, for example, U.S. Pat. No. 4,582,815, the entire contents of which are incorporated herein by reference.

As an alternative to forming self-bound catalysts, zeolite crystals can be combined with a binder, such as, for example, one or more of $Al_2O_3$, $TiO_2$, $ZrO_2$, $SiO_2$, $SiO_2/Al_2O_3$, and MgO to form bound catalysts. Generally, a binder can be present in an amount between about 1 wt. % and about 90 wt. %, for example between about 3 wt. % and about 90 wt. % of a catalyst, about 3 wt. % to about 80 wt. %, about 5 wt. % to about 90 wt. %, about 5 wt. % to about 80 wt. %, about 5 wt. % to about 40 wt. %, or about 10 wt. % to about 40 wt. %. In some embodiments, the catalyst can include at least about 5 wt. % binder, for example at least about 10 wt. %, or at least about 20 wt. %. Additionally, or alternately, the catalyst can include about 90 wt. % or less of binder, for example about 80 wt. % or less, about 50 wt. % or less, about 40 wt. % or less, or about 35 wt. % or less. Combining the zeolite and the binder can generally be achieved, for example, by mulling a mixture of the zeolite and binder (optionally an aqueous mixture) and then extruding the mixture into catalyst pellets.

In some embodiments, a binder for formulating a catalyst can be selected so that the resulting bound catalyst has a micropore surface area of at least about 290 $m^2/g$, for example at least about 300 $m^2/g$ or at least about 310 $m^2/g$. Optionally but preferably, a suitable binder can be a binder with a surface area of about 200 $m^2/g$ or less, for example about 175 $m^2/g$ or less or about 150 $m^2/g$ or less. Unless otherwise specified, the surface area of the binder is defined herein as the combined micropore surface area and mesopore surface area of the binder.

The zeolite employed in the present conversion catalyst generally comprises at least one medium pore aluminosilicate zeolite having a Constraint index of 1-12 (as defined in U.S. Pat. No. 4,016,218). Suitable zeolites include zeolites having an MFI or MEL framework, such as ZSM-5 or ZSM-11. ZSM-5 is described in detail in U.S. Pat. Nos. 3,702,886 and RE29,948. ZSM-11 is described in detail in U.S. Pat. No. 3,709,979. Preferably, the zeolite is ZSM-5. Other useful zeolites can include ZSM-12 (U.S. Pat. No. 3,832,449); ZSM-22 (U.S. Pat. No. 4,556,477); ZSM-23 (U.S. Pat. No. 4,076,842); ZSM-34 (U.S. Pat. No. 4,079,095) ZSM-35 (U.S. Pat. No. 4,016,245); ZSM-48 (U.S. Pat. No. 4,397,827); ZSM-57 (U.S. Pat. No. 4,046,685); and ZSM-58 (U.S. Pat. No. 4,417,780). Non-limiting examples of SAPO and AlPO molecular sieves can include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, and AlPO-46.

Another option for characterizing a zeolite or other molecular sieve is based on the nature of the ring channels in the zeolite. The ring channels in a zeolite can be defined based on the number of atoms including in the ring structure that forms the channel. In some embodiments, a zeolite can include at least one ring channel based on a 10-member ring. In such aspects, the zeolite preferably does not have any ring channels based on a ring larger than a 10-member ring. Examples of suitable framework structures having a 10-member ring channel but not having a larger size ring channel include EUO, FER, IMF, LAU, MEL, MFI, MFS, MTT, MWW, NES, PON, SFG, STF, STI, TON, TUN, MRE, and PON framework types.

In some alternative embodiments, the zeolite can be a molecular sieve that includes an 8-member ring channel (small pore molecular sieves), a 10-member ring channel (as described above), or a 12-member ring channel (large pore molecular sieves), but does not have any ring channels based on a ring larger than a 12-member ring. In such aspects, suitable large pore molecular sieves can include those having AFI, AFS, ATO, ATS, *BEA, BEC, BOG, BPH, CAN, CON, EMT, EON, EZT, FAU, GME, GON, IFR, ISV, -*ITN, IWR, IWW, LTL, MAZ, MEI, MOR, MOZ, MSE, MTW, OFF, OKO, OSI, SAF, SAO, SEW, SFE, SFO, SSF, SSY, and USI framework types. In such aspects, suitable small pore molecular sieves can include those having the AEI, AFT, AFX, ATT, DDR, EAB, EPI, ERI, KFI, LEV, LTA, MER, MON, MTF, PAU, PHI, RHO, and SFW framework types.

Generally, a zeolite having the desired activity can have a silicon to aluminum molar ratio of about 10 to about 300, for example about 15 to about 100, about 20 to about 80, or about 20 to about 40. In some embodiments, the silicon to aluminum ratio can be at least about 10, for example at least about 20, at least about 30, at least about 40, at least about 50, or at least about 60. Additionally, or alternatively, the silicon to aluminum ratio can be about 300 or less, for example about 200 or less, about 100 or less, about 80 or less, about 60 or less, or about 50 or less.

In some preferred embodiments, the silicon to aluminum ratio can be at least about 20, for example at least about 30 or at least about 40. In such embodiments, the silicon to aluminum ratio can optionally be about 100 or less, for example about 80 or less, about 60 or less, about 50 or less, or about 40 or less. Typically, reducing the silicon to aluminum ratio in a zeolite can result in a zeolite with a higher acidity, and therefore higher activity for cracking of hydrocarbon or hydrocarbonaceous feeds, such as petroleum feeds. With respect to conversion of alcohols and/or ethers to olefins, such increased cracking activity due to a decrease in the silicon to aluminum ratio may result in increased formation of residual carbon or coke during the conversion reaction. Such residual carbon can deposit on the zeolite conversion catalyst, leading to a change in the properties of the catalyst over time. Having a silicon to aluminum ratio of at least about 40, for example at least about 50 or at least about 60, can reduce/minimize the amount of additional residual carbon formed due to the acidic or cracking activity of the conversion catalyst.

It is noted that the molar ratio described herein is a ratio of silicon to aluminum. If a corresponding ratio of silica to alumina were described, the corresponding ratio of silica ($SiO_2$) to alumina ($Al_2O_3$) would be twice as large, due to the presence of two aluminum atoms in each alumina stoichiometric unit compare to only one silicon atom in the silica stoichiometric unit. Thus, a silicon to aluminum ratio of 10 corresponds to a silica to alumina ratio of 20.

In some optional aspects, the zeolite conversion catalyst employed herein can further be characterized by at least one, at least two, or all three of the following properties: (a) a mesoporosity of greater than about 20 $m^2/g$, for example greater than about 30 $m^2/g$, and less than about 120 $m^2/g$, for example less than about 100 $m^2/g$ or less than about 85 $m^2/g$; (b) a microporous surface area of at least about 290 $m^2/g$, for example at least about 300 $m^2/g$ or at least about 310 $m^2/g$; and (c) a diffusivity for 2,2-dimethylbutane of greater than about $1.0 \times 10^{-2}$ $sec^{-1}$, for example greater than about $1.25 \times 10^{-2}$ $sec^{-1}$, when measured at a temperature of about 120° C. and a 2,2-dimethylbutane pressure of about 60 ton (about 8 kPa).

Additionally, or alternatively, a conversion catalyst may have a combined micropore and mesopore surface area of at least about 30 $m^2/g$, for example at least about 50 $m^2/g$.

Of these properties, mesoporosity and diffusivity for 2,2-dimethylbutane can be determined by several factors for a given zeolite, including the crystal size of the zeolite. Microporous surface area is determined by the pore size of the zeolite and the availability of the zeolite pores at the surfaces of the catalyst particles. Producing a zeolite conversion catalyst with the desired minimum mesoporosity, microporous surface area and 2,2-dimethylbutane diffusivity should be well within the expertise of anyone of ordinary skill in zeolite chemistry. It is noted that mesopore or external surface area and micropore surface area can be characterized, for example, using adsorption-desorption isotherm techniques within the expertise of one of skill in the art, such as the BET (Brunauer Emmett Teller) method.

It is noted that the micropore surface area can be characterized for either zeolite crystals or a catalyst formed from the zeolite crystals. In various aspects, the micropore surface area of a self-bound catalyst or a catalyst formulated with a separate binder can be at least about 340 $m^2/g$, for example at least about 350 $m^2/g$, at least about 360 $m^2/g$, at least about 370 $m^2/g$, or at least about 380 $m^2/g$. Typically, a formulation of zeolite crystals into catalyst particles (either self-bound or with a separate binder) can result in some loss of micropore surface area relative to the micropore surface area of the zeolite crystals. Thus, to provide a catalyst having the desired micropore surface area, the zeolite crystals can also have a micropore surface area of at least about 290 $m^2/g$, for example at least about 300 $m^2/g$, or at least about 310 $m^2/g$. As a practical matter, the micropore surface area of a zeolite crystal and/or a corresponding self-bound or bound catalyst as described herein can be less than about 1000 $m^2/g$, and typically less than about 750 $m^2/g$. Additionally or alternately, the micropore surface area of a catalyst (self-bound or with a separate binder) can be about 105% or less of the micropore surface area of the zeolite crystals in the catalyst, and typically about 100% or less of the micropore surface area of the zeolite crystals in the catalyst, for example from about 80% to 100% of the micropore surface area of the zeolite crystals in the catalyst. In some embodiments, the micropore surface area of a catalyst can be at least about 80% of the micropore surface area of the zeolite crystals in the catalyst, for example at least about 85%, at least about 90%, at least about 95%, at least about 97%, or at least about 98%, and/or about 100% or less, for example about 99% or less, about 98% or less, about 97% or less, or about 95% or less.

Additionally, or alternatively, the diffusivity for 2,2-dimethylbutane of a catalyst (self-bound or with a separate binder) can be about 105% or less of the diffusivity for 2,2-dimethylbutane of the zeolite crystals in the catalyst, and typically about 100% or less of the diffusivity for 2,2-dimethylbutane of the zeolite crystals in the catalyst, for example about 80% to 100% of the diffusivity for 2,2-dimethylbutane of the zeolite crystals in the catalyst. In some embodiments, the diffusivity for 2,2-dimethylbutane of a catalyst can be at least about 80% of the diffusivity for 2,2-dimethylbutane of the zeolite crystals in the catalyst, for example at least about 85%, at least about 90%, at least about 95%, at least about 97%, or at least about 98%, and/or about 100% or less, for example about 99% or less, about 98% or less, about 97% or less, or about 95% or less.

When used in the present conversion catalyst, the zeolite can be present at least partly in the hydrogen (active) form. Depending on the conditions used to synthesize the zeolite, this may correspond to converting the zeolite from, for example, the sodium form. This can readily be achieved, for example, by ion exchange to convert the zeolite to the ammonium form followed by calcination in air or an inert atmosphere at a temperature of about 400° C. to about 700° C. to convert the ammonium form to the active hydrogen form. Alternatively, methods for directly converting a sodium form zeolite to a hydrogen form zeolite can also be used. Such methods are well known to the person of ordinary skill in the art.

Additionally, or alternatively, the conversion catalyst can include and/or be enhanced by one or more metals selected from groups 1 to 14 of the periodic table.

The metal can be incorporated into the zeolite by any convenient method known in the art, such as by impregnation or by ion exchange. After impregnation or ion exchange, the metal-enhanced catalyst may be treated in air or an inert atmosphere at a temperature of about 400° C. to about 700° C. The amount of metal can be related to the molar amount of aluminum present in the zeolite. In some embodiments, the molar amount of the metal can correspond to about 0.1 to about 1.3 times the molar amount of aluminum in the zeolite. In some embodiments, the molar amount of metal can be at least about 0.1 times the molar amount of aluminum in the zeolite, for example at least about 0.2 times, at least about 0.3 times, or at least about 0.4 times. Additionally, or alternatively, the molar amount of metal can be about 1.3 times or less relative to the molar amount of aluminum in the zeolite, for example about 1.2 times or less, about 1.0 times or less, or about 0.8 times or less. Still further additionally or alternately, the amount of metal can be expressed as a weight percentage of the conversion catalyst, such as having at least about 0.1 wt. % of metal, at least about 0.25 wt. %, at least about 0.5 wt. %, at least about 0.75 wt. %, or at least about 1.0 wt. %. Additionally, or alternatively, the amount of metal can be about 20 wt. % or less, for example about 10 wt. % or less, about 5 wt. % or less, about 2.0 wt. % or less, about 1.5 wt. % or less, about 1.2 wt. % or less, about 1.1 wt. % or less, or about 1.0 wt. % or less.

In some embodiments, the conversion catalyst can include one or more metals from groups 12 to 14 of the periodic table and thus include the metal zinc. In additional or alternate embodiments, the conversion catalyst can include one or more metals from groups 1 and 2 of the periodic table. The total weight of the metals can be about 0.1 wt. % to about 10.0 wt. % based on the total weight of the conversion catalyst. Thus, the upper limit on the range of metals in the conversion catalyst may be 10.0 wt. %, 9.0 wt. %, 8.0 wt. %, 7.0 wt. %, 6.0 wt. %, 5.0 wt. %, 4.0 wt. %, 3.0 wt. %, 2.0 wt. %, or 1.0 wt. %; and the lower limit on the range may be 9.0 wt. %, 8.0 wt. %, 7.0 wt. %, 6.0 wt. %, 5.0 wt. %, 4.0 wt. %, 3.0 wt. %, 2.0 wt. %, 1.0 wt. %, or 0.1 wt. %. Ranges expressly disclosed include combinations of any of the above-enumerated upper and lower limits, e.g., 0.1 to 10.0 wt. %, 0.1 to 8.0 wt. %, 0.1 to 6.0 wt. %, 0.1 to 5.0 wt. %, 0.1 to 4.0 wt. %, 0.1 to 3.0 wt. %, 0.1 to 2.0 wt. %, 0.1 to 1.0 wt. %, 1.0 to 10.0 wt. %, 1.0 to 9.0 wt. %, 1.0 to 8.0 wt. %, 1.0 to 7.0 wt. %, 1.0 to 6.0 wt. %, 1.0 to 5.0 wt. %, 1.0 to 4.0 wt. %, 1.0 to 3.0 wt. %, etc.

To form a metal-enhanced conversion catalyst, a self-bound (or bound) catalyst can, for example, be impregnated via incipient wetness with a solution containing the desired metal for impregnation, such as one or more of Zn, Ga, B, Ca, Ti, V, Fe, Cu, Mo, Ru, Pd, Rh, Ir, Nb, W, Re, and Pt. The impregnated catalyst can then be dried overnight at about 120° C., followed by calcination in air for about 3 hours at about 540° C. More generally, a transition metal can be incorporated into the ZSM-5 crystals and/or catalyst at any convenient time, such as before or after ion exchange to form H-ZSM-5 crystals, or before or after formation of an extrudate. In some embodiments that are preferred from a standpoint of facilitating manufacture of a zeolite catalyst, the transition metal can be incorporated into the catalyst (such as by impregnation or ion exchange) after formation of the catalyst by extrusion or another convenient method.

In some embodiments, the conversion catalyst can be substantially free of phosphorous. A conversion catalyst that is substantially free of phosphorous can contain no more than about 0.01 wt. % of phosphorous, for example less than about 0.005 wt. % of phosphorous or less than about 0.001 wt. % of phosphorous. A conversion catalyst that is substantially free of phosphorous can be substantially free of intentionally added phosphorous or substantially free of both intentionally added phosphorous as well as phosphorous present as an impurity in a reagent for forming the conversion catalyst. In some embodiments, the conversion catalyst can contain no added phosphorous, such as containing no intentionally added phosphorous and/or containing no phosphorous impurities to within the detection limits of standard methods for characterizing a reagent and/or a resulting conversion catalyst.

In other aspects, the conversion catalyst can include phosphorus. The total weight of the phosphorous can be from about 0.1 wt. % to about 10.0 wt. % based on the total weight of the conversion catalyst. Thus, the upper limit on the range of the phosphorous present in the conversion catalyst may be 10.0 wt. %, 9.0 wt. %, 8.0 wt. %, 7.0 wt. %, 6.0 wt. %, 5.0 wt. %, 4.0 wt. %, 3.0 wt. %, 2.0 wt. %, or 1.0 wt. %; and the lower limit on the range may be 9.0 wt. %, 8.0 wt. %, 7.0 wt. %, 6.0 wt. %, 5.0 wt. %, 4.0 wt. %, 3.0 wt. %, 2.0 wt. %, 1.0 wt. %, or 0.1 wt. %. Ranges expressly disclosed include combinations of any of the above-enumerated upper and lower limits, e.g., 0.1 to 10.0 wt. %, 0.1 to 8.0 wt. %, 0.1 to 6.0 wt. %, 0.1 to 5.0 wt. %, 0.1 to 4.0 wt. %, 0.1 to 3.0 wt. %, 0.1 to 2.0 wt. %, 0.1 to 1.0 wt. %, 1.0 to 10.0 wt. %, 1.0 to 9.0 wt. %, 1.0 to 8.0 wt. %, 1.0 to 7.0 wt. %, 1.0 to 6.0 wt. %; 1.0 to 5.0 wt. %, 1.0 to 4.0 wt. %, 1.0 to 3.0 wt. % etc. Of course, the total weight of the phosphorous shall not include amounts attributable to the zeolite itself, if the zeolite contains any phosphorus.

The yield of olefins relative to the total hydrocarbons in the alcohol conversion product may be 10 wt. % to 95 wt. %, or 15 wt. % to 90 wt. %, or 20 wt. % to 90 wt. %, or 30 wt. % to 90 wt. %, or 40 wt. % to 90 wt. %, or 20 wt. % to 80 wt. %, or 30 wt. % to 80 wt. %, or 20 wt. % to 70 wt. %, or 20 wt. % to 60 wt. %, or 20 wt. % to 50 wt. %.

Additionally, or alternatively, the yield of aromatics relative to the total hydrocarbons in the conversion product may be 0.1 wt. % to 50 wt. %, 0.5 wt. % to 40 wt. %, or 1 wt. % to 30 wt. %, or 1 wt. % to 20 wt. % or 1 wt. % to 10 wt. % or 1 wt. % to 5 wt. %.

Additionally, or alternatively, the yield of paraffins relative to the total hydrocarbon product may be 5 wt. % to 50 wt. %, or 5 wt. % to 40 wt. %, or 5 wt. % to 30 wt. % or 5 wt. % to 20 wt. % or 10 wt. % to 40 wt. % or 10 wt. % to 30 wt. %

Additionally, or alternatively, the yield of C3+ olefins relative to the total hydrocarbon product may be 10 wt. % or more, or 15 wt. % or more, or 20 wt. % or more, or 25 wt. % or more, or 30 wt. % or more, or 35 wt. % or more.

Additionally, or alternatively, the yield of C4+ olefins relative to the total hydrocarbon product may be 10 wt. % or more, or 15 wt. % or more, or 20 wt. % or more, or 25 wt. % or more, or 30 wt. % or more, or 35 wt. % or more.

In the claims below, the relative amounts of paraffins, olefins, and aromatics in a sample can be determined based on ASTM D6839.

Suitable and/or effective conditions for performing a conversion reaction may include average reaction temperatures of 200° C. to 550° C. (or 250° C. to 550° C., or 300° C. to 550° C., or 350° C. to 550° C., or 400° C. to 500° C.), total pressures between 10 psig (~70 kPa-g) to 400 psig (~2700 kPa-g), or 50 psig (~350 kPa-g) to 350 psig (~2400 kPa-g), or 100 psig (~700 kPa-g) to 300 psig (~2100 kPa-g), and an alcohol space velocity between 0.1 h$^{-1}$ to 10 h$^{-1}$ based on weight of alcohol relative to weight of catalyst. For example, the average reaction temperature may be at least 200° C., or at least 250° C., or at least 300° C., or at least 350° C., or at least 400° C., or at least 450° C. Additionally or alternately, the average reaction temperature can be 550° C. or less, or 500° C. or less, or 450° C. or less, or 400° C. or less. In this specification, average reaction temperature is defined as the average of the temperature at the reactor inlet and the temperature at the reactor outlet for the reactor where the conversion reaction is performed. In some embodiments, where lower pressures are used, the pressure can correspond to 70 kPa-g to 700 kPa-g. As another example, the total pressure can be at least 70 kPa-g, or at least 350 kPa-g, or at least 500 kPa-g, or at least 700 kPa-g, or at least 1000 kPa-g. Additionally or alternately, the total pressure can be 3000 kPa-g or less, or 2700 kPa-g or less, or 2400 kPa-g or less, or 2100 kPa-g or less.

Various types of reactors may provide a suitable configuration for performing a conversion reaction. Suitable reactors may include fixed bed reactors, moving bed reactors, fluidized bed reactors, and riser reactors.

It is noted that the activity and/or selectivity of the herein disclosed conversion catalysts for alcohol and/or ether conversion may vary as the conversion catalysts are exposed to increasing amounts of alcohol and/or ether feed. The variation may occur, for example, because of build-up of coke in the conversion catalyst. In some embodiments, a feature of the presently disclosed processes is that the average residence time of conversion catalyst in a reaction zone may be controlled through withdrawal of at least some of the conversion catalyst from the reaction zone, regeneration of the conversion catalyst in a regeneration zone, and return of the regenerated conversion catalyst to the reaction zone. The average residence time may be selected to control conversion catalyst activity, alcohol and/or ether conversion and product selectivity so as to maximize yields of particular products.

In embodiments where a conversion catalyst can be removed from the reaction zone for regeneration and recycle during operation in a reactor, such as a moving bed reactor, a fluidized bed reactor or a riser reactor, conversion catalyst can be removed, regenerated in a regeneration zone and the regenerated conversion catalyst returned to the reaction zone.

The regeneration zone may be a reactor operated as a fixed bed, a fluidized bed, an ebulating bed, a settling bed, a riser reactor or a combination thereof. In practice, the regeneration zone may include a plurality of reactors, such as a plurality of riser reactors connected in parallel. The regeneration zone should be operated at the minimum temperature required to remove the required amount of coke at the design residence time and in particular the temperature should not exceed the point at which metal oxide volatilization occurs or the conversion catalyst substrate undergoes rapid deterioration. Typically, regeneration zone temperature is from about 400° C. to about 700° C., such as from about 550° C. to about 650° C. Catalyst residence time in the regeneration zone also should be minimized to reduce catalyst aging rate and maximize percent of time the catalyst spends in the reactor doing useful work. In embodiments, the average residence time of catalyst particles in the regeneration zone may be between 0.1 and 100 minutes, or between 1 and 20 minutes.

In some embodiments, the alcohol feed and/or conversion reaction environment can include water in various proportions. Conversion of alcohol to olefins results in production of water as a product, so the relative amounts of alcohol and water can vary within the reaction environment.

While only conventional separation schemes are likely required in the herein disclosed processes (e.g. distillation, adsorption with molecular sieves, liquid-liquid extraction), the person of ordinary skill in the art would appreciate that these separations may be performed in a multitude of ways depending on how the process is designed.

In the present disclosure, reference to 'separation' of process streams may refer to one or more distillative separations, wherein components are separated based on boiling point or adsorption with molecular sieves/membrane based on size or polarity.

FIG. 1 illustrates a proposed process scheme for ethanol conversion to olefins over an ethanol conversion catalyst as disclosed herein. Feed stream 100, comprising ethanol, is fed to reactor 105 which contains an olefin conversion catalyst. The effluent 110 which comprises olefins is fed to separator 115 which removes water as stream 125 and provides hydrocarbon stream 120. The hydrocarbon stream is fed to further separator 130 which separates the hydrocarbons into olefin rich stream 135 and stream 140 which contains aromatics and paraffins. The olefin rich stream is sent to further separator 145 which separates the heavier C3+ olefins 155 from ethylene 150. The ethylene may be sent to oligomerization reactor 160 to provide higher olefin stream 165.

The C3+ olefins may be oligomerized in oligomerization unit 170 to afford higher olefins which may be fed via 175 to hydrogenator 180 to yield stream 185 comprising jet or diesel fuels.

In separator 115 about 39.1 wt. % of products that are water (based on the mass content of the hydroxyl group plus a proton from ethanol) are separated from the hydrocarbons.

EXAMPLES

A suitable self-bound ZSM-5 (SB-ZSM-5) for use in the herein disclosed processes may be prepared according to the method described in paragraph [0045] of United States Patent Application Publication No. 20150175897.

Example 1

Preparation of 0.5% Zn Self-Bound ZSM-5

About 20 g of SB-ZSM-5 extrudate was measured for its water absorption factor and determined to be about 0.62. 0.46 g of $Zn(NO_3)_2\ 6H_2O$ was added to 11.94 g $H_2O$. The resulting solution was slowly added to the SB-ZSM-5 in a pill coater set to 30 rpm by slowly spraying in the Zn solution over 5 min. The resulting extrudate was mixed for 20 min at 10 rpm, held at ambient temperature for 1 h, and then dried in an oven at 175° C. overnight. The extrudate was further dried in flowing dry air at 500° C. for 3 h, producing 18.8 g total 0.5% Zn SB-ZSM-5.

Example 2

Conversion of ethanol to olefins with SB-ZSM-5

Ethanol conversion experiments were performed in a ~10 cc reactor, with a fixed bed of ~2 g zeolite catalyst diluted in sand. The ethanol was 100% ethanol. The ethanol feed rate was 5 cc/h for all experiments, and pressure was varied during the runs are described below. The WHSV for all experiments was ~2.

SB-ZSM-S catalyst was contacted with ethanol in the fixed bed reactor operating at 350° C. or 450° C. and at a pressure between about 15 and about 50 psig. The ethanol was fed to the zeolite catalyst bed and the effluent from the bed periodically analyzed for product composition.

Ethanol conversion was ~100% throughout the runs.

Gas phase analysis was performed with an online GC. The liquid products were separated by density into aqueous and hydrocarbon components. The aqueous phase was analyzed by density measurement and the hydrocarbon phase was analyzed by GC.

Figure 2:
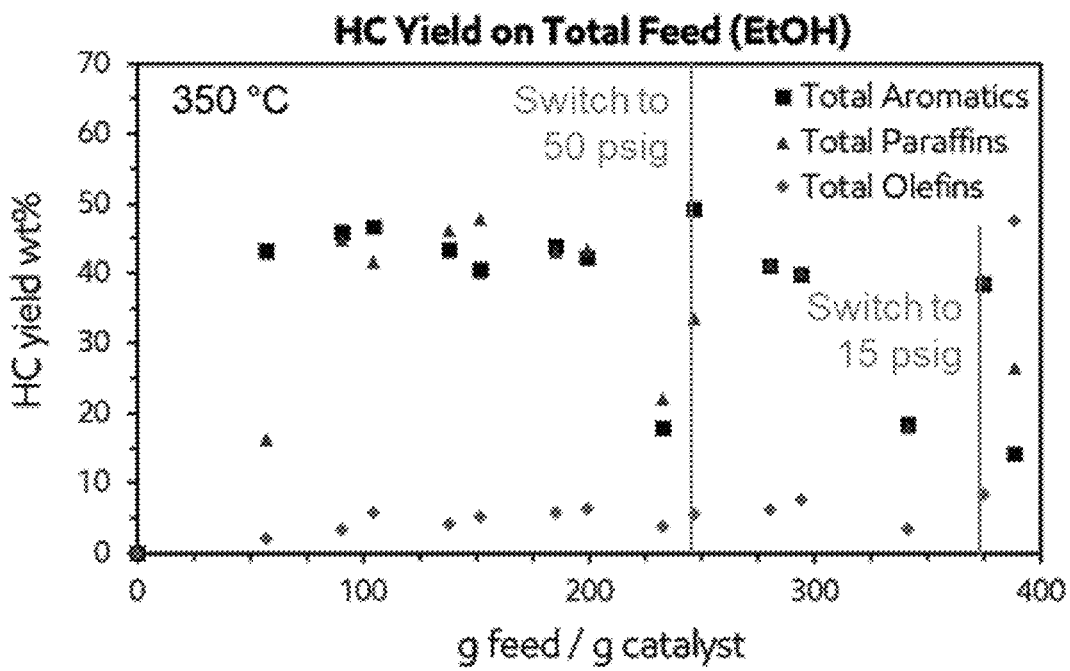
FIG. 2 is a graph showing total hydrocarbon (HC) yields for aromatics, paraffins, and olefins over SB-ZSM-5 at 350° C.
Figure 3:
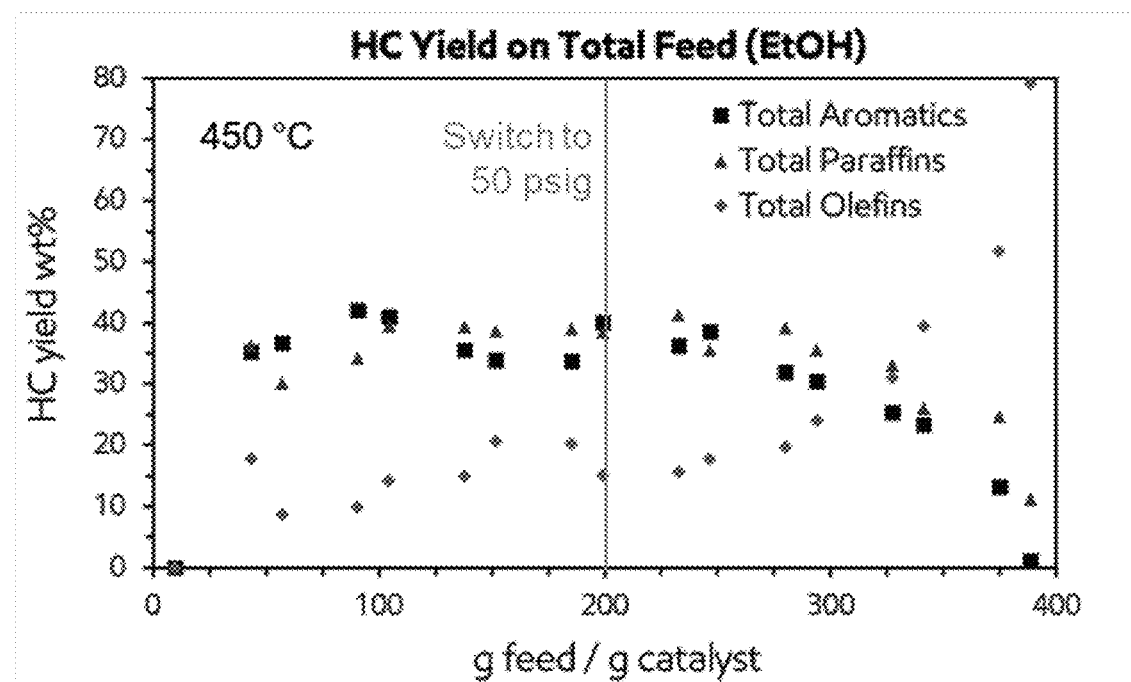
FIG. 3 is a graph showing total hydrocarbon (HC) yields for aromatics, paraffins, and olefins over SB-ZSM-5 at 450° C.

A summary of the conditions is presented in Table 1. FIGS. 2 and 3 illustrate the weight % hydrocarbon yield against gram ethanol feed per gram catalyst (g/g) at 350° C. and 450° C. respectively.

TABLE 1

| Temperature | Pressure |
|---|---|
| 350 | 15 psig |
|  | 50 psig at 247 g/g |
| 450 | 15 psig |
|  | 50 psig at 200 g/g |

During both runs the pressure was increased from 15 psig to 50 psig and for the 350° C. run the pressure was decreased back to 15 psig. These pressure changes appeared to have a limited effect on the product composition. In FIG. 2 at 350° C., olefin production was <10% of total hydrocarbons produced throughout the run, with aromatics and paraffins dominating product composition. This product split remained relatively constant throughout the run.

At 450° C. in FIG. 3, olefin production at 100% ethanol conversion was approximately double that at 350° C., with a commensurate decrease in aromatics and paraffins production. After the pressure change to 50 psig, olefins production began to increase, ultimately reaching 80% of the total products at 389 g feed/g catalyst. This could be caused by the pressure increase or catalyst coking, which may be expected to occur more rapidly at higher temperatures.

Figure 4:
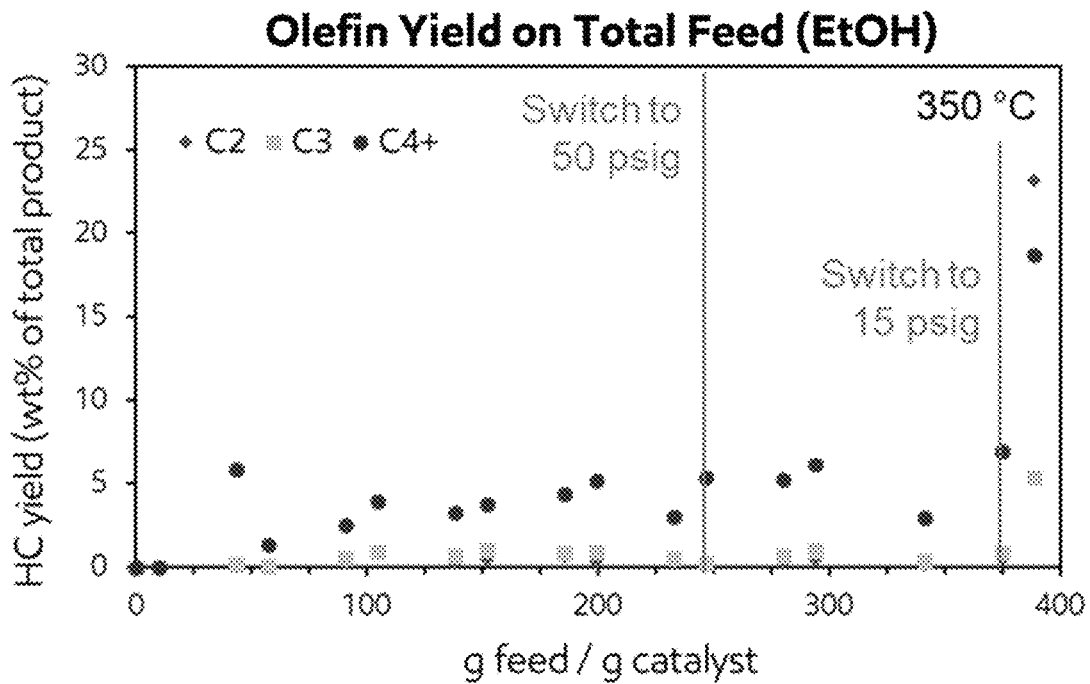
FIG. 4 is a graph showing olefin yields as a percent of the total hydrocarbon product for SB-ZSM-5 at 350° C.
Figure 5:
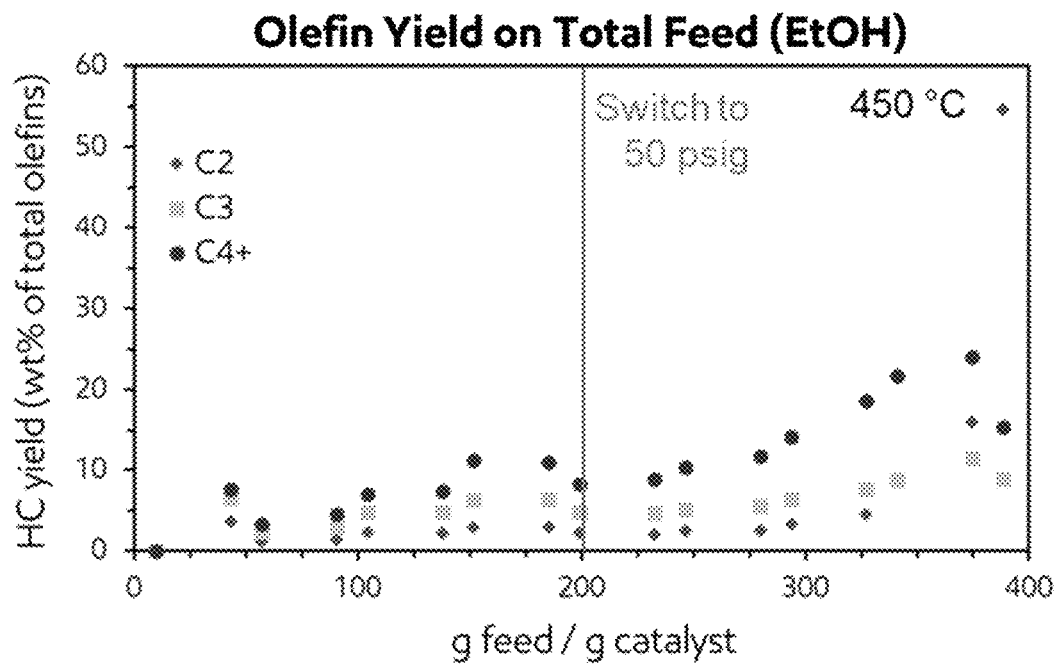
FIG. 5 is a graph showing olefin yields as a percent of the total hydrocarbon product for SB-ZSM-5 at 450° C.

Yields for different olefinic products in each run are illustrated in FIGS. 4 (350° C.) and 5 (450° C.). At 350° C., despite the low overall yield toward olefins, the primary component of the olefinic fraction of the products is C3+ olefins, with limited production of propylene within this fraction.

At 450° C., overall olefin production is significantly higher than at 350° C., with an increase in the production of ethylene. After the pressure change to 50 psig, the olefin production rises rapidly, with ethylene coming to be the primary product at 389 g feed/g catalyst. Significantly, C3 olefins are observed in non-zero quantities. It might be expected that olefins with an even carbon number would be favored due to the addition of C2 units, however this did not appear to be the case. It is possible to produce olefinic products with an odd carbon number through cracking, which is possibly how these products were produced, but the percentage of propylene in the products from SB-ZSM-5 at 450° C. was surprising.

Narula C. K. et al (Scientific Reports volume 5, Article number: 16039, 2015) describe the conversion of ethanol to olefins over an InV-ZSM-5 zeolite. A comparison between the published results for this catalyst and the present SB-ZSM-5 results is shown in Table 2.

TABLE 2

| Catalyst | InV-ZSM-5 360° C. | SB-ZSM-5 350° C. |
|---|---|---|
| Olefins % | 6.5 | 6.3 |
| Paraffins % | 33.2 | 43.4 |
| Aromatics % | 60.2 | 42.7 |
| Unknowns % | — | 7.6 |

From the results, it is evident that in terms of olefin production, the present SB-ZSM-5 is close to the InV-ZSM-5 zeolite, while advantageously absent the metals indium and vanadium.

Figure 6:
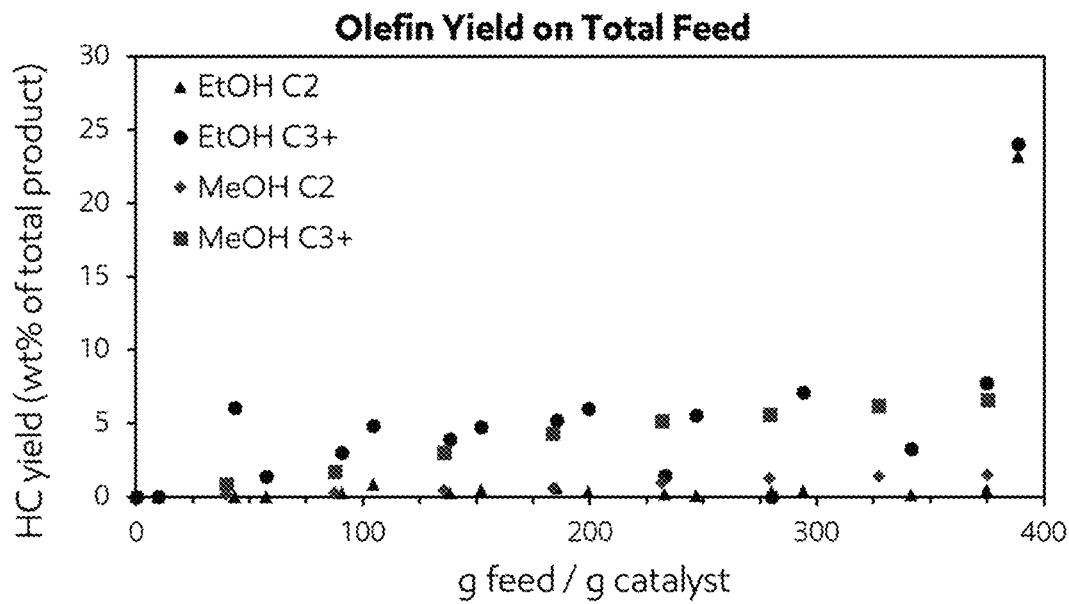
FIG. 6 is a graph comparing ethanol and methanol conversion to olefins at 350° C., broken down by ethylene and higher olefins (C3+).

Overall, the conversion of ethanol resulted in approximately equivalent paraffins production, higher aromatics production, and slightly lower olefins production than methanol. The comparison of the olefin yields for ethanol and methanol indicates similar results at 350° C. (FIG. 6).

Figure 7:
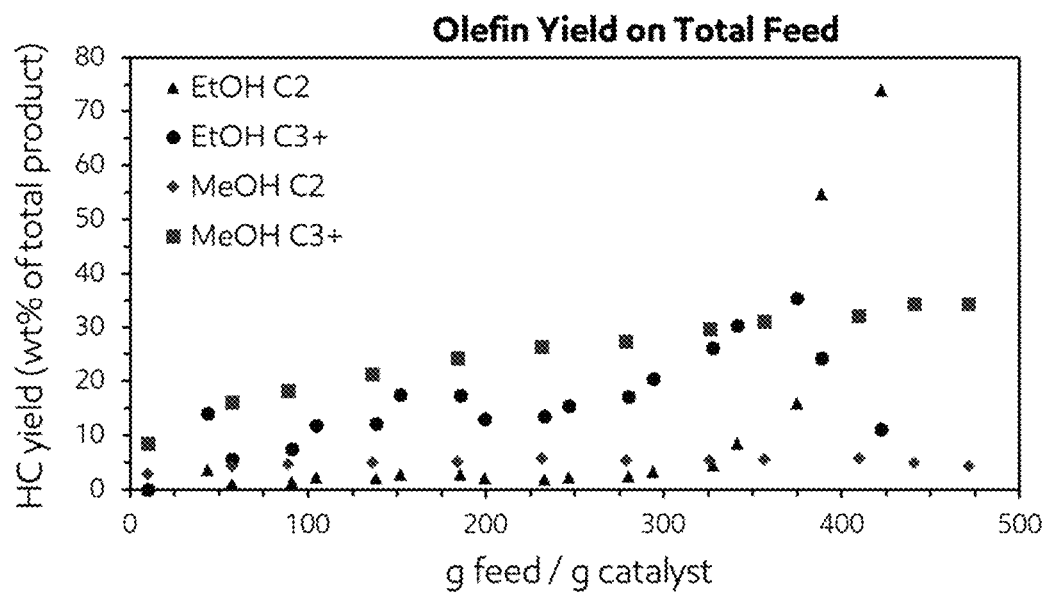
FIG. 7 is a graph comparing ethanol and methanol conversion to olefins at 450° C., broken down by ethylene and higher olefins (C3+).

At 450° C. (FIG. 7), the comparative performance of ethanol and methanol changes significantly. Methanol produces more olefins in total for most of the run time, with about 10 percentage points more C3+ olefin production than ethanol for the initial portion of the run. Toward the end of each run, methanol production shows approximately steady production (a decrease is likely at longer run times as more coke is produced in the catalyst), while for ethanol, C3+ olefin production drops significantly while ethylene production increases rapidly. This is again likely the result of the preformed C—C bond in the feed ethanol, leading to extensive ethylene production late in the catalyst lifetime, as dehydration of ethanol to ethylene is fast relative to the requirement for the formation of C—C bonds.

Example 3

Conversion of Ethanol to Olefins with 0.5% Zn SB-ZSM-5

A sample of SB-ZSM-5 with 0.5% Zn by weight prepared as in Example 1, was tested to determine the extent to which metal loading impacts the conversion of ethanol to olefins.

Figure 8:
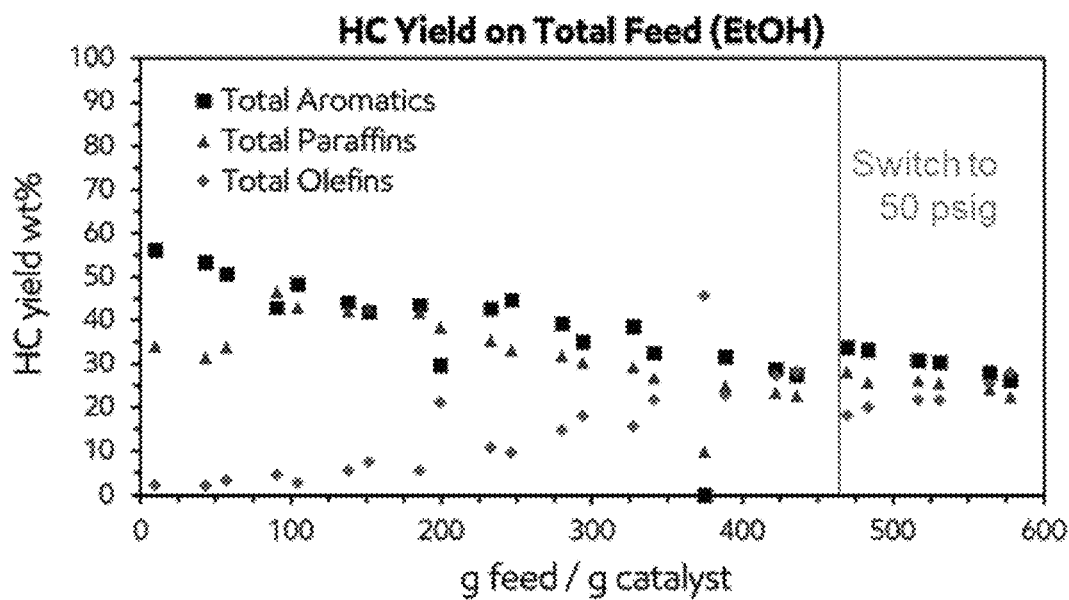
FIG. 8 is a graph showing total hydrocarbon (HC) yields for aromatics, paraffins, and olefins over 0.5% Zn SB-ZSM-5 at 350° C.

At 350° C. (FIG. 8), initial production was primarily aromatics and paraffins, with limited olefin production. However, as time on stream increased, both aromatics and paraffins declined while olefin production increased until they were all approximately equivalent wt. % products. After a pressure switch to 50 psig at 469 g feed/g catalyst, aromatics production increased with a commensurate decrease in olefins production, but shortly after this olefins production again increased to surpass that of either aromatics or paraffins. Liquid hydrocarbons were collected throughout the experiment, up to and including the final mass balance at 578 g feed/g catalyst.

Figure 9:
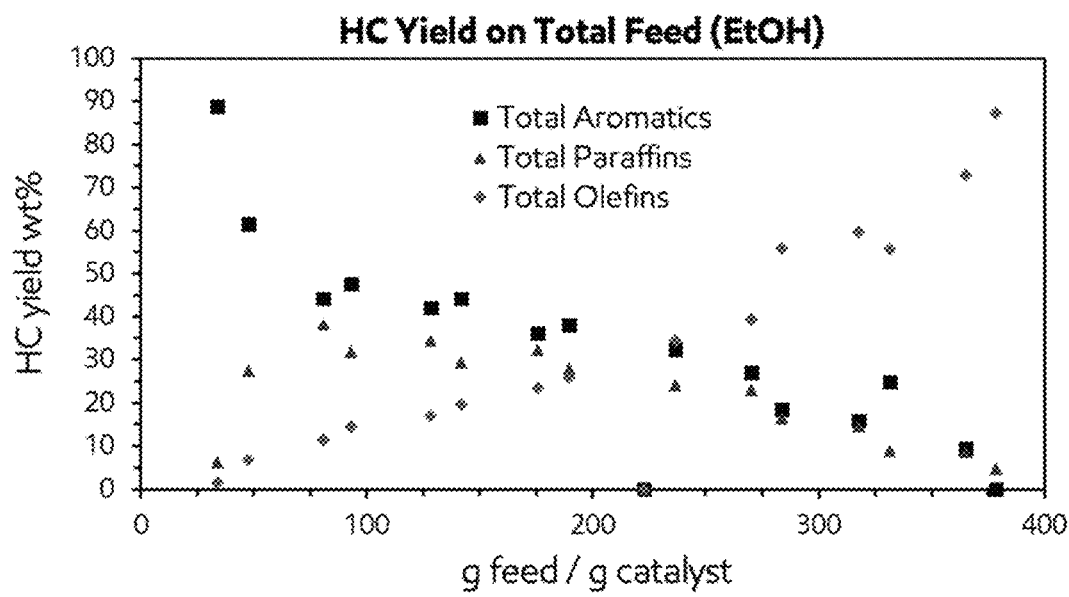
FIG. 9 is a graph showing total hydrocarbon (HC) yields for aromatics, paraffins, and olefins over 0.5% Zn SB-ZSM-5 at 450° C.

For the same experiment at 450° C., the same general trends (FIG. 9) hold true with initial primarily aromatics production followed by significantly increased olefins production as the run progressed, but the magnitudes are different. The first mass balance showed nearly 90 wt. % aromatics production, compared to ~55 wt. % at 350° C. Furthermore, at 375 g feed/g catalyst, olefin production increased to nearly 90% of total hydrocarbon production. It is notable that after 400 g feed/g catalyst, essentially no liquid hydrocarbon product was produced, and it was significantly less in each mass balance throughout the experiment as compared to the data at 350° C.

These experiments provided several significant results. One is the high initial selectivity toward aromatics; in the widely-accepted mechanism for methanol conversion on zeolites, hydrogen transfer reactions from higher olefins are required to get molecules into the so-called aromatics carbon pool, producing an alkane along the way. This very high selectivity toward aromatics is possibly the result of easy access to higher olefins (as ethanol dehydration to ethylene is fast, followed by olefin methylation/ethylation steps to higher olefins), coupled with facile hydrogen transfer reactions to the aromatics pool.

Figure 10:
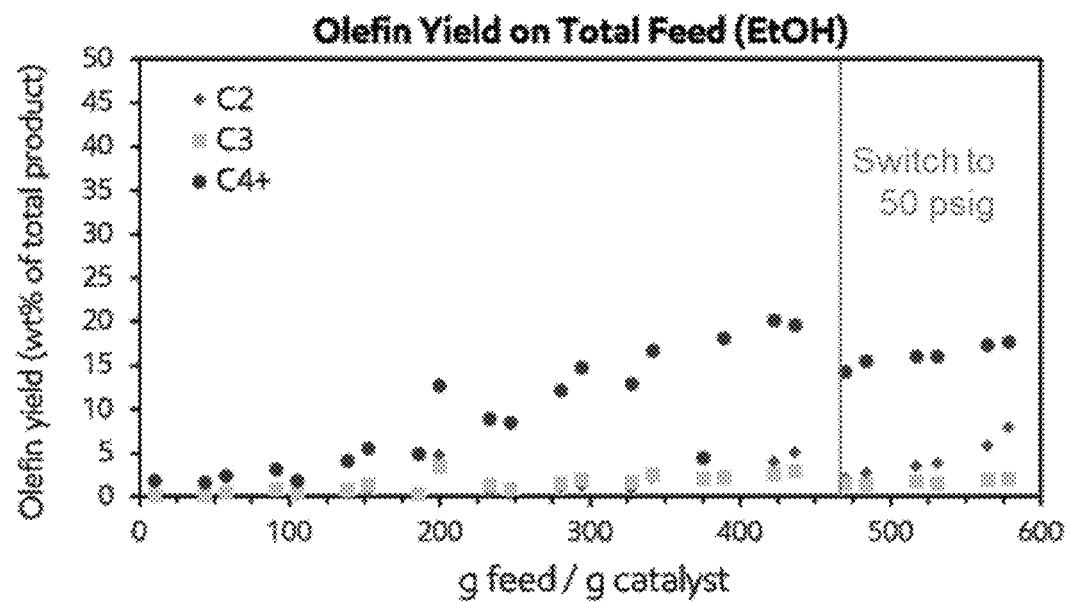
FIG. 10 is a graph showing olefin yields as a percent of the total hydrocarbon product for 0.5% Zn SB-ZSM-5 at 350° C.

Another significant result is that, while olefin yields were only in the range of 2-20 wt. % HC yield for most the run at 350° C., selectivity within those products was very high for C4+ olefins (FIG. 10). The increase in total olefin production that begins around 140 g feed/g catalyst is also primarily driven by an increase in C4+ olefins, with a much smaller increase for ethylene and propylene. This is likely driven by the starting C2 unit of ethanol, leading to fast reaction to higher olefins. As the reaction progresses, the relative rates of olefin methylation/ethylation to hydrogen transfer (prior to cyclization to aromatics) increase, leading to an increase in higher olefins in the hydrocarbon products.

Figure 11:
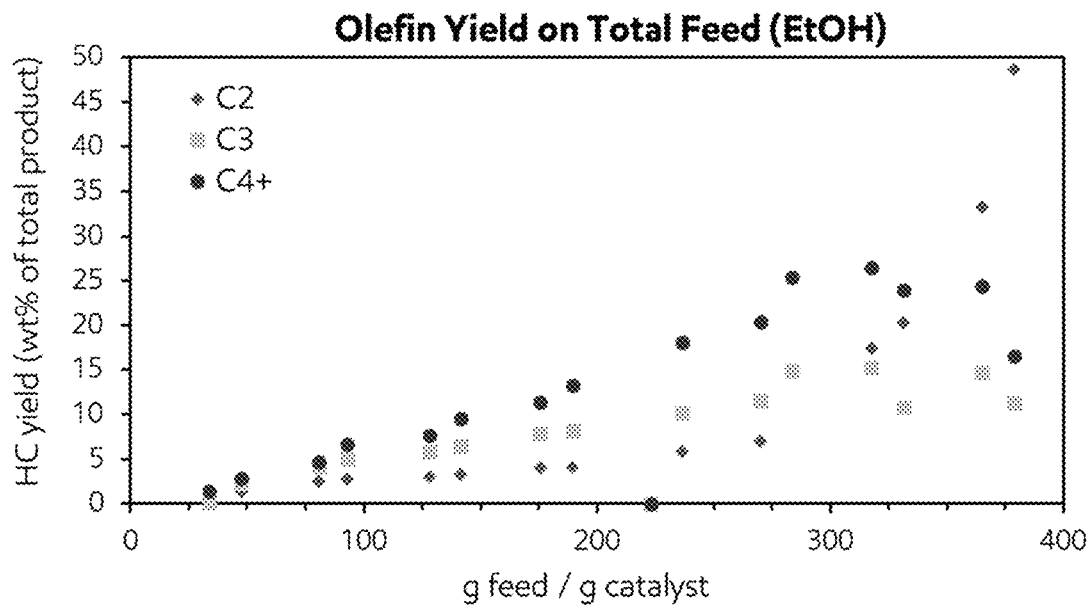
FIG. 11 is a graph showing olefin yields as a percent of the total hydrocarbon product for 0.5% Zn SB-ZSM-5 at 450° C.

Olefin yields at 450° C. were both higher and distributed differently than those at 350° C. (FIG. 11). While C4+ olefins were still the primary olefinic product, it was not as large of a percentage of the total olefins as at 350° C. However, significant propylene, up to 15 wt. % of the total hydrocarbon product, was produced along with the up to 25 wt. % C4+, leading to high overall yields of higher olefins. Beyond 300 g feed/g catalyst, ethylene became the dominant olefinic product.

However, considering the use of a moving bed reactor, a specific product slate can in theory be chosen based on the rate of regeneration of the catalyst, leading to the ability to pick an operating window that would, in this case, maximize the production of C3+ olefins (essentially, the point at about 280 g feed/g catalyst).

In Table 3 below, the "optimal" conditions for producing olefins at each temperature are shown for SB-ZSM-5 and 0.5% Zn SB-ZSM-5. Given the potential to choose operating conditions and an operating window with a moving bed reactor, these yields could be achievable in an actual process. In the Table, P, A, and O refer to paraffins, aromatics and olefins, respectively.

TABLE 3

| Temperature (° C.) | SB ZSM-5 % product | | 0.5% Zn ZSM-5 % product | |
|---|---|---|---|---|
| | P/A/O | C3 + olefins | P/A/O | C3 + olefins |
| 350 | 42/45/5 | 5 | 23/29/27 | 24 |
| 450 | 39/34/20 | 12 | 9/25/56 | 40 |

Example 4

Conversion of 1-Butanol to Olefins with 0.5% Zn SB-ZSM-5

A sample of SB-ZSM-5 with 0.5% Zn by weight prepared as in Example 1 was tested in the conversion of 1-butanol to olefins.

1-Butanol conversion experiments were performed in a ~10 cc reactor, with a fixed bed of ~2 g zeolite catalyst diluted in sand. 1-Butanol feed rate was 5 cc/h and the WHSV was ~2.

The catalyst was contacted with 1-butanol in the fixed bed reactor operating at 450° C. and at a pressure of about 15 psig. The 1-butanol was fed to the zeolite catalyst bed and the effluent from the bed periodically analyzed for product composition.

Gas phase analysis was performed with an online GC. The liquid products were separated by density into aqueous and hydrocarbon components. The aqueous phase was analyzed by density measurement and the hydrocarbon phase was analyzed by GC.

Figure 12:
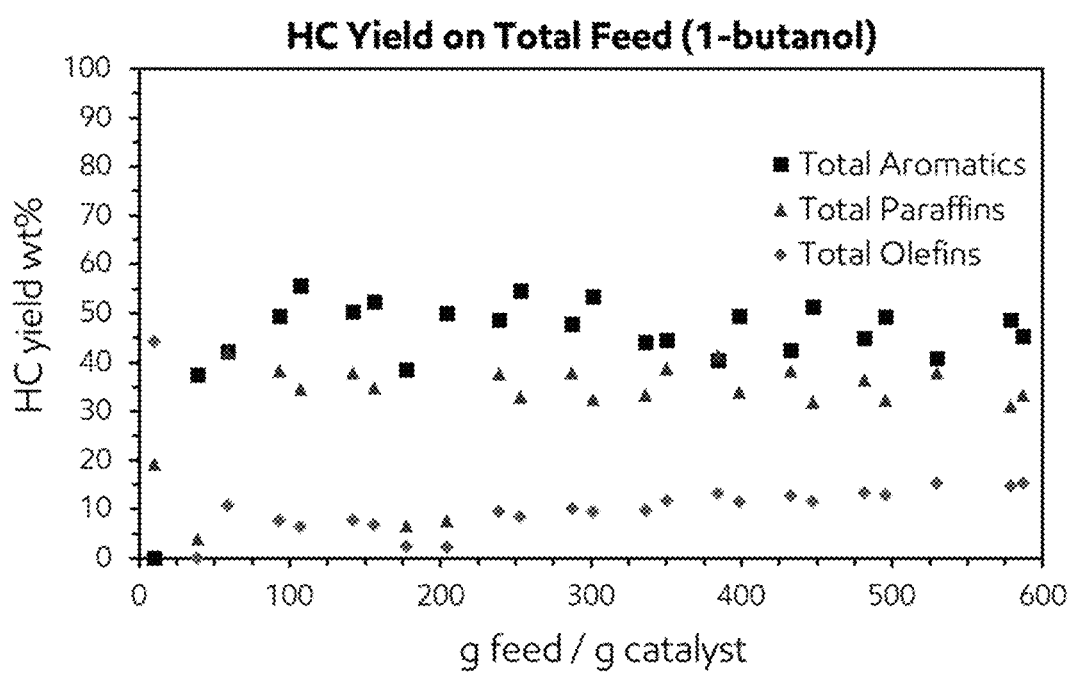
FIG. 12 is a graph showing total hydrocarbon (HC) yields for aromatics, paraffins, and olefins over 0.5% Zn SB-ZSM-5 at 450° C. based on a 1-butanol feed.
Figure 13:
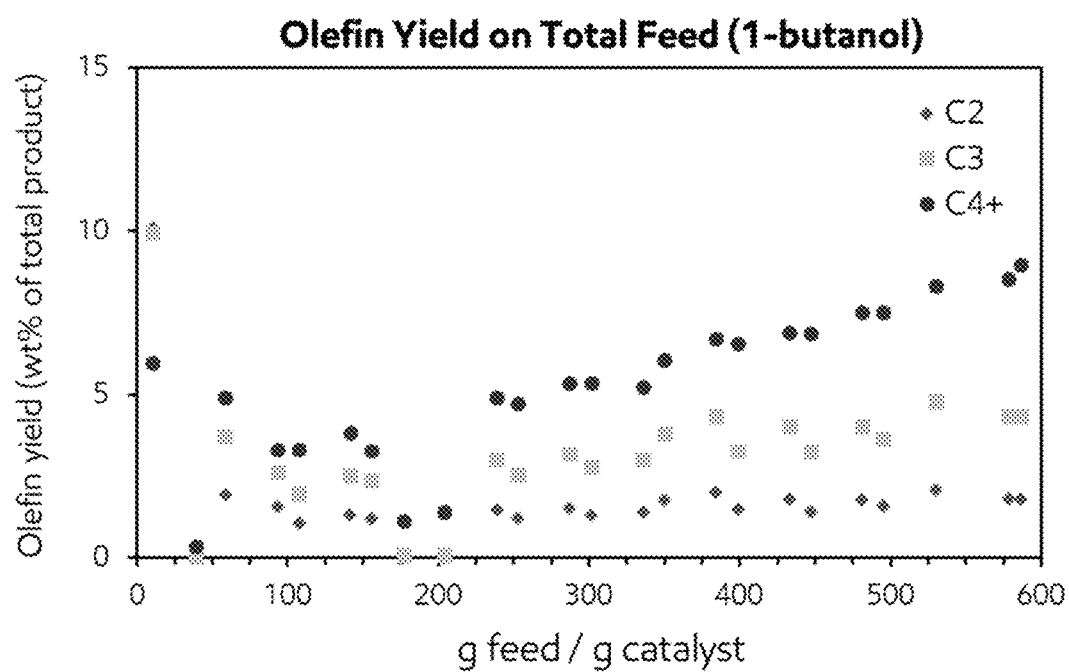
FIG. 13 is a graph showing olefin yields as a percent of the total hydrocarbon product for 0.5% Zn SB-ZSM-5 at 450° C. based on a 1-butanol feed.

FIG. 12 illustrates the weight % hydrocarbon yield against gram 1-butanol feed per gram catalyst (g/g) and FIG. 13 the olefin yields at 450° C.

FIG. 12 indicates that throughout the experiment, aromatics accounted for about 50% of the products. Mass balances were typically in the range of 93-105% and indicated that the conversion of 1-butanol was relatively complete, as it was not significantly present in the aqueous layer (based on the density of 1.00 g/cm$^3$) and was also not found in significant quantities in the products, given the mass balance closures of the total aromatics, paraffins, and olefins.

Referring to FIG. 13 the distribution of olefinic products can give some insight into the nature of the process occurring during the reaction of 1-butanol. While the overall percentages of olefins were not particularly high, the C4+ olefin percentages were quite high compared to lower olefins, especially as the catalyst was exposed to more feed. This preference for higher order olefins is likely the result of the 1-butanol containing a C4 unit. Cracking is required to produce ethylene and propylene, resulting in their reduced production relative to higher olefins.

Certain Embodiments

Certain embodiments of processes according to the present disclosure are presented in the following paragraphs.

Embodiment 1 provides a process for converting alcohols and/or ethers to olefins, said process comprising:
contacting a feed comprising one or more alcohols and/or one or more ethers with a conversion catalyst in a reaction zone at a temperature from about 200° C. to about 550° C. under conditions effective to produce an olefin-containing effluent, the olefin-containing effluent comprising 10 wt. % or more of olefins and 60 wt. % or less of aromatics relative to a weight of hydrocarbons in the olefin-containing effluent, the olefin-containing effluent comprising 5 wt. % or more of C3+ olefins relative to a weight of hydrocarbons in the olefin-containing effluent, the conversion catalyst comprising a zeolite framework structure.

Embodiment 2 provides a process according to embodiment 1, wherein the wt. % of olefins relative to the weight of hydrocarbons in the olefin-containing effluent is 15 wt. % or more, or 20 wt. % or more, or 25 wt. % or more, or 30 wt. % or more, or 35 wt. % or more, or 40 wt. %, or more or 45 wt. % or more, or 50 wt. % or more, or 55 wt. % or more.

Embodiment 3 provides a process according to embodiment 1 or embodiment 2, wherein the wt. % of aromatics relative to the weight of hydrocarbons in the olefin-containing effluent is 40 wt. % or less, or 35 wt. % or less, or 30 wt. % or less, or 25 wt. % or less.

Embodiment 4 provides a process according to any one of embodiments 1 to 3, wherein the wt. % of C3+ olefins relative to the weight of hydrocarbons in the olefin-containing effluent is 10 wt. % or more, or 15 wt. % or more, or 20 wt. % or more, or 25 wt. % or more, or 30 wt. % or more, or 35 wt. % or more.

Embodiment 5 provides a process according to any one of embodiments 1 to 4, wherein the wt. % of C4+ olefins relative to the weight of hydrocarbons in the olefin-containing effluent is 10 wt. % or more, or 15 wt. % or more, or 20 wt. % or more, or 25 wt. % or more, or 30 wt. % or more, or 35 wt. % or more.

Embodiment 6 provides a process according to any one of embodiments 1 to 5, wherein the wt. % of paraffins relative to the weight of hydrocarbons in the olefin-containing effluent is 45 wt. % or less, or 40 wt. % or less, or 35 wt. % or less, or 30 wt. % or less, or 25 wt. % or less, or 20 to wt. % or less, or 15 wt. % or less, or 10 wt. % or less.

Embodiment 7 provides a process according to any one of embodiments 1 to 6, wherein the contacting occurs at a temperature from about 250° C. to about 500° C.

Embodiment 8 provides a process according to any one of embodiments 1 to 7, wherein the contacting occurs at a pressure from about 5 psig to about 400 psig.

Embodiment 9 provides a process according to any one of embodiments 1 to 8, wherein the WHSV is from about 0.1 h−1 to about 10 h−1.

Embodiment 10 provides a process according to any one of embodiments 1 to 9, wherein the conversion catalyst comprises a MFI type zeolite.

Embodiment 11 provides a process according to any one of embodiments 1 to 10, wherein the conversion catalyst comprises ZSM-5 or silicalite.

Embodiment 12 provides a process according to any one of embodiments 1 to 11, wherein the conversion catalyst is a self-bound catalyst.

Embodiment 13 provides a process according to any one of embodiments 1 to 12, wherein the conversion catalyst further comprises about 1 wt. % to about 40 wt. % of a binder comprising one or more of $Al_2O_3$, $TiO_2$, $ZrO_2$, $SiO_2$, $SiO_2/Al_2O_3$ and MgO, based on the total weight of the conversion catalyst.

Embodiment 14 provides a process according to any one of embodiments 1 to 13, wherein the conversion catalyst further comprises about 0.1 wt. % to about 20 wt. % of one or more metals selected from groups 1 to 14 of the periodic table.

Embodiment 15 provides a process according to embodiment 14, wherein the one or more metals comprise one or more of Zn, Ga, B, Ca, Ti, V, Fe, Cu, Mo, Ru, Pd, Rh, Ir, Nb, W, Re, and Pt.

Embodiment 16 provides a process according to embodiment 14, wherein the conversion catalyst further comprises about 0.1 wt. % to about 20 wt. % of one or more metals selected from groups 12 to 14 of the periodic table.

Embodiment 17 provides a process according to embodiment 14, wherein the conversion catalyst further comprises about 0.1 wt. % to about 5 wt. % of one or more metals selected from groups 12 to 14 of the periodic table.

Embodiment 18 provides a process according to embodiment 14, wherein the conversion catalyst comprises Zn.

Embodiment 19 provides a process according to embodiment 18, wherein the conversion catalyst comprises about 0.1 wt. % to about 2 wt. % Zn.

Embodiment 20 provides a process according to any one of embodiments 1 to 19, wherein the reaction zone comprises one or more of a fixed bed reactor, a fluidized bed reactor, a riser reactor, and a moving bed reactor.

Embodiment 21 provides a process according to any one of embodiments 1 to 20, wherein the reaction zone comprises one or more moving bed reactors.

Embodiment 22 provides a process according to embodiment 20 or embodiment 21, further comprising a step of transferring at least a portion of the conversion catalyst to a regeneration zone, separate from the reaction zone, and contacting the conversion catalyst with a regeneration gas in the regeneration zone to at least partially remove coke deposited on the conversion catalyst in the reaction zone, whereby the conversion catalyst is at least partially regenerated, and then returning the thus at least partially regenerated conversion catalyst to the reaction zone.

Embodiment 23 provides a process according to embodiment 22, wherein the regeneration gas comprises oxygen, for example, air.

Embodiment 24 provides a process according to embodiment 22 or embodiment 23, wherein the at least partially regenerated conversion catalyst is returned to the reaction zone at a rate sufficient to produce an olefin-containing effluent comprising 10 wt. % or more of C3+ olefins, relative the weight of hydrocarbons in the olefin-containing effluent Embodiment 25 provides a process according to any one of embodiments 22 to 24, wherein the at least partially regenerated conversion catalyst is returned to the reaction zone at a rate sufficient to produce an olefin-containing effluent comprising 15 wt. % or more of C3+ olefins, or 20 wt. % or more, or 25 wt. % or more, or 30 wt. % or more, or 35 wt. % or more, relative the weight of hydrocarbons in the olefin-containing effluent.

Embodiment 26 provides a process according to any one of embodiments 22 to 25, wherein the at least partially regenerated conversion catalyst is returned to the reaction zone at a rate sufficient so that 1 gram of conversion catalyst is, on average, exposed to at least 200 gram of feed in the reaction zone.

Embodiment 27 provides a process according to any one of embodiments 22 to 26, wherein the at least partially regenerated conversion catalyst is returned to the reaction zone at a rate sufficient so that 1 gram of conversion catalyst is, on average, exposed to at least 300 gram of feed, or at least 400 gram of feed, or at least 500 gram of feed in the reaction zone.

Embodiment 28 provides a process according to any one of embodiments 22 to 27, wherein the at least partially regenerated conversion catalyst is returned to the reaction zone at a rate sufficient to afford an average degree of conversion catalyst coking within the reaction zone to produce an olefin-containing effluent comprising 10 wt. % or more of C3+ olefins, relative the weight of hydrocarbons in the olefin-containing effluent.

Embodiment 29 provides a process according to any one of embodiments 22 to 28, wherein the at least partially regenerated conversion catalyst is returned to the reaction zone at a rate sufficient to afford an average degree of conversion catalyst coking within the reaction zone to produce an olefin-containing effluent comprising 15 wt. % or more of C3+ olefins, or 20 wt. % or more, or 25 wt. % or more, or 30 wt. % or more, or 35 wt. % or more, relative the weight of hydrocarbons in the olefin-containing effluent.

Embodiment 30 provides a process according to any one of embodiments 22 to 29, wherein the regeneration zone is a riser reactor, a moving bed reactor or fixed bed reactor.

Embodiment 31 provides a process according to any one of embodiments 1 to 30, wherein the one or more alcohols comprise one or more of ethanol, 1-propanol, 2-propanol, 1-butanol and 2-butanol.

Embodiment 32 provides a process according to any one of embodiments 1 to 31, wherein the one or more alcohols are derived from fermentation or bio-conversion.

Embodiment 33 provides a process according to any one of embodiments 1 to 32, wherein the feed comprising one or more alcohols comprises at least 5% by weight of the one or more alcohols.

Embodiment 34 provides a process according to any one of embodiments 1 to 33, wherein the feed comprising one or more alcohols further comprises water.

Embodiment 35 provides a process according to any one of embodiments 1 to 30, wherein the one or more ethers comprise one or more of diethyl ether, di-n-propyl ether, di-iso-propyl ether, di-n-butyl ether and di-iso-butyl ether.

Embodiment 36 provides a process according to any one of embodiments 1 to 35, further comprising the step of separating water from the olefin-containing effluent.

Embodiment 37 provides a process according to any one of embodiments 1 to 36, further comprising the step of separating at least some of the olefin-containing effluent to provide a stream rich in olefins.

Embodiment 38 provides a process according to embodiment 37, further comprising the step of separating at least some of the stream rich in olefins to provide at least a stream rich in ethylene and a stream rich in C3+ olefins.

Embodiment 39 provides a process according to embodiment 38, wherein the stream rich in ethylene is further oligomerized.

Embodiment 40 provides a process according to embodiment 38, wherein at least some of the C3+ olefins are oligomerized to higher olefins.

Embodiment 41 provides a process according to embodiment 40, wherein at least some of the higher olefins are hydrogenated to jet or diesel fuels.

The contents of all references and published patents and patent applications cited throughout the application are hereby incorporated by reference.

It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

What is claimed is:

1. A process for converting alcohols and/or ethers to olefins, said process comprising:
    contacting a feed comprising one or more alcohols and/or one or more ethers with a conversion catalyst in a reaction zone at a temperature from about 200° C. to about 550° C. under conditions effective to produce an olefin-containing effluent,
    wherein the olefin-containing effluent comprises 10 wt. % or more of olefins and 60 wt. % or less of aromatics relative to a weight of hydrocarbons in the olefin-containing effluent, and
    wherein the conversion catalyst comprises a self-bound zeolite including a transition metal yielding a selectivity of about 35% or greater C3+ olefins between 250° C. and 450° C.

2. A process according to claim 1, wherein the wt. % of olefins relative to the weight of hydrocarbons in the olefin-containing effluent is 15 wt. % or more.

3. A process according to claim 1, wherein the wt. % of aromatics relative to the weight of hydrocarbons in the olefin-containing effluent is 40 wt. % or less.

4. A process according to claim 1, wherein the wt. % of C3+ olefins relative to the weight of hydrocarbons in the olefin-containing effluent is 10 wt. % or more.

5. A process according to claim 1, wherein the wt. % of C4+ olefins relative to the weight of hydrocarbons in the olefin-containing effluent is 10 wt. % or more.

6. A process according to claim 1, wherein the wt. % of paraffins relative to the weight of hydrocarbons in the olefin-containing effluent is 45 wt. % or less.

7. A process according to claim 1, wherein the contacting occurs at a temperature from about 250° C. to about 500° C.

8. A process according to claim 1, wherein the contacting occurs at a pressure from about 5 psig to about 400 psig.

9. A process according to claim 1, wherein the WHSV is from about 0.1 h$^{-1}$ to about 10 h$^{-1}$.

10. A process according to claim 1, wherein the conversion catalyst comprises a MFI type zeolite.

11. A process according to claim 1, wherein the conversion catalyst comprises ZSM-5 or silicalite.

12. A process according to claim 1, wherein the conversion catalyst further comprises about 0.1 wt. % to about 20 wt. % of an additional one or more metals selected from groups 1 to 14 of the periodic table.

13. A process according to claim 1, wherein the conversion catalyst comprises the transition metal in an amount of about 0.1 wt. % to about 20 wt. % and wherein the transition metal is selected from groups 12 to 14 of the periodic table.

14. A process according to claim 1, wherein the conversion catalyst comprises Zn.

15. A process according to claim 1, wherein the reaction zone comprises one or more of a fixed bed reactor, a fluidized bed reactor, a riser reactor, and a moving bed reactor.

16. A process according to claim 1, wherein the reaction zone comprises one or more moving bed reactors.

17. A process according to claim 16, further comprising a step of transferring at least a portion of the conversion catalyst to a regeneration zone, separate from the reaction zone, and contacting the conversion catalyst with a regeneration gas in the regeneration zone to at least partially remove coke deposited on the conversion catalyst in the reaction zone, whereby the conversion catalyst is at least partially regenerated, and then returning the thus at least partially regenerated conversion catalyst to the reaction zone.

18. A process according to claim 1, wherein the one or more alcohols comprise one or more of ethanol, 1-propanol, 2-propanol, 1-butanol and 2-butanol.

19. A process according to claim 1, wherein the one or more alcohols are derived from fermentation or bio-conversion.

20. A process according to claim 1, wherein the feed comprising one or more alcohols comprises at least 5% by weight of the one or more alcohols.

21. A process according to claim 1, wherein the feed comprising one or more alcohols further comprises water.

22. A process according to claim 1, wherein the one or more ethers comprise one or more of diethyl ether, di-n-propyl ether, di-iso-propyl ether, di-n-butyl ether and di-iso-butyl ether.

23. A process according to claim 1, further comprising the step of separating water from the olefin-containing effluent.

24. A process according to claim 1, further comprising the step of separating at least some of the olefin-containing effluent to provide a stream rich in olefins.

* * * * *